United States Patent
Matusz et al.

(10) Patent No.: US 8,932,979 B2
(45) Date of Patent: Jan. 13, 2015

(54) CATALYST COMPOSITION, A PROCESS FOR PREPARING THE CATALYST COMPOSITION AND A USE OF THE CATALYST COMPOSITION

(75) Inventors: Marek Matusz, Houston, TX (US); Michael Alan Richard, Fulshear, TX (US); Martin Lysle Hess, Fulshear, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 12/191,949

(22) Filed: Aug. 14, 2008

(65) Prior Publication Data
US 2008/0306289 A1 Dec. 11, 2008

Related U.S. Application Data

(63) Continuation of application No. 10/815,089, filed on Mar. 31, 2004, now abandoned.

(60) Provisional application No. 60/459,136, filed on Mar. 31, 2003.

(51) Int. Cl.
| | | |
|---|---|---|
| *B01J 27/25* | (2006.01) | |
| *B01J 23/00* | (2006.01) | |
| *B01J 23/02* | (2006.01) | |
| *B01J 23/06* | (2006.01) | |
| *A01N 37/20* | (2006.01) | |
| *A01N 37/34* | (2006.01) | |
| *A01N 37/40* | (2006.01) | |
| *A01N 47/46* | (2006.01) | |
| *A01N 47/48* | (2006.01) | |
| *B01J 21/04* | (2006.01) | |
| *B01J 23/68* | (2006.01) | |
| *C07C 233/76* | (2006.01) | |
| *C07C 235/46* | (2006.01) | |
| *C07C 255/57* | (2006.01) | |
| *C07C 331/12* | (2006.01) | |
| *C07C 331/20* | (2006.01) | |
| *C07D 301/10* | (2006.01) | |
| *B01J 35/10* | (2006.01) | |

(52) U.S. Cl.
CPC .............. *A01N 37/20* (2013.01); *A01N 37/34* (2013.01); *A01N 37/40* (2013.01); *A01N 47/46* (2013.01); *A01N 47/48* (2013.01); *B01J 21/04* (2013.01); *B01J 23/688* (2013.01); *C07C 233/76* (2013.01); *C07C 235/46* (2013.01); *C07C 255/57* (2013.01); *C07C 331/12* (2013.01); *C07C 331/20* (2013.01); *C07D 301/10* (2013.01); *B01J 35/1009* (2013.01)

USPC ........... 502/201; 502/241; 502/259; 502/335; 502/340; 502/344; 502/349

(58) Field of Classification Search
USPC ......... 502/201, 241, 259, 263, 335, 340, 344, 502/349
See application file for complete search history.

(56) References Cited

U.S. PATENT DOCUMENTS

| | | | |
|---|---|---|---|
| 3,893,910 A | 7/1975 | Robson | 208/138 |
| 3,962,136 A | 6/1976 | Nielsen et al. | 252/454 |
| 4,010,115 A | 3/1977 | Nielsen et al. | 252/454 |
| 4,012,425 A | 3/1977 | Nielsen et al. | 260/348 |
| 4,039,561 A | 8/1977 | Mitsuhata et al. | 260/348.34 |
| 4,212,772 A | 7/1980 | Mross et al. | 252/476 |
| 4,226,782 A | 10/1980 | Hayden et al. | 260/348.34 |
| 4,356,312 A | 10/1982 | Nielsen et al. | 549/534 |
| 4,419,222 A | 12/1983 | Grenoble et al. | 208/120.1 |
| 4,761,394 A | 8/1988 | Lauritzen | 502/348 |
| 4,766,105 A | 8/1988 | Lauritzen | 502/216 |
| 4,808,738 A | 2/1989 | Lauritzen | 549/536 |
| 4,820,675 A | 4/1989 | Lauritzen | 502/216 |
| 4,822,900 A | 4/1989 | Hayden | 549/534 |
| 4,845,296 A | 7/1989 | Ahmed et al. | 564/477 |

(Continued)

FOREIGN PATENT DOCUMENTS

| | | | |
|---|---|---|---|
| EP | 003642 | | 8/1979 |
| EP | 266015 | A1 | 5/1988 |

(Continued)

OTHER PUBLICATIONS

Kirk-Othmer Ency. of Chem. Tech., 3rd Ed., vol. 9 (1980); pp. 445-447.

*Primary Examiner* — Shuangyi Abu Ali

(57) ABSTRACT

A catalyst composition comprising a support having a surface area of at least 500 m$^2$/kg, and deposited on the support:
- silver metal,
- a metal or component comprising rhenium, tungsten, molybdenum or a nitrate- or nitrite-forming compound, and
- a Group IA metal or component comprising a Group IA metal having an atomic number of at least 37, and in addition potassium, wherein the value of the expression $(Q_K/R)+Q_{HIA}$ is in the range of from 1.5 to 30 mmole/kg, wherein $Q_{HIA}$ and $Q_K$ represent the quantities in mmole/kg of the Group IA metal having an atomic number of at least 37 and potassium, respectively, present in the catalyst composition, the ratio of $Q_{HIA}$ to $Q_K$ is at least 1:1, the value of $Q_K$ is at least 0.01 mmole/kg, and R is a dimensionless number in the range of from 1.5 to 5, the units mmole/kg being relative to the weight of the catalyst composition.

21 Claims, No Drawings

(56) References Cited

U.S. PATENT DOCUMENTS

| | | | |
|---|---|---|---|
| 4,908,343 A | 3/1990 | Bhasin | 502/218 |
| 4,916,243 A | 4/1990 | Bhasin et al. | 549/534 |
| 5,012,027 A | 4/1991 | Abrevaya et al. | 585/443 |
| 5,057,481 A | 10/1991 | Bhasin | 502/208 |
| 5,100,859 A | 3/1992 | Gerdes et al. | 502/439 |
| 5,106,802 A | 4/1992 | Horiuchi et al. | 502/65 |
| 5,380,697 A | 1/1995 | Matusz et al. | 502/348 |
| 5,504,053 A * | 4/1996 | Chou et al. | 502/348 |
| 5,739,075 A | 4/1998 | Matusz | 502/302 |
| 5,801,259 A | 9/1998 | Kowaleski | 549/536 |
| 5,965,481 A | 10/1999 | Durand et al. | 502/304 |
| 6,251,820 B1 | 6/2001 | Tsuji | 502/242 |
| 6,368,998 B1 | 4/2002 | Lockemeyer | 502/347 |
| 6,498,259 B1 | 12/2002 | Grey et al. | 549/533 |
| 6,504,053 B1 | 1/2003 | Chaturvedi et al. | 502/348 |
| 6,511,938 B1 | 1/2003 | Liu et al. | 502/347 |
| 6,534,441 B1 | 3/2003 | Bartley et al. | 502/337 |
| 6,579,825 B2 | 6/2003 | Lockemeyer | 503/347 |
| 2002/0010094 A1 | 1/2002 | Lockemeyer | 502/439 |

FOREIGN PATENT DOCUMENTS

| | | |
|---|---|---|
| EP | 716884 | 12/1995 |
| GB | 1594362 | 7/1981 |
| JP | 50-095213 | 7/1975 |
| JP | 56-105750 | 8/1981 |
| WO | WO 0015333 | 3/2000 |
| WO | WO 0015334 | 3/2000 |
| WO | WO 0015335 | 3/2000 |

* cited by examiner

US 8,932,979 B2

CATALYST COMPOSITION, A PROCESS FOR PREPARING THE CATALYST COMPOSITION AND A USE OF THE CATALYST COMPOSITION

REFERENCE TO PRIOR APPLICATIONS

This application is a continuation application of U.S. patent application Ser. No. 10/815,089, filed on Mar. 31, 2004, now abandoned which claims the benefit of U.S. Provisional Application No. 60/459,136, filed on Mar. 31, 2003, which applications are incorporated herein by reference in their entirety.

FIELD OF THE INVENTION

The invention relates to a catalyst composition suitable for the epoxidation of ethylene, a process for preparing the catalyst composition and a process for the epoxidation of ethylene in which the catalyst composition is used.

BACKGROUND OF THE INVENTION

The catalytic epoxidation of ethylene using a silver-based catalyst has been practiced for a long time. However, conventional silver-based catalysts have provided ethylene oxide notoriously in a low selectivity. For example, when using conventional catalysts, the selectivity towards ethylene oxide, expressed as a fraction of the ethylene converted, does not reach values above the 6/7 or 85.7 mole-% limit. Therefore, this limit has long been considered to be the theoretically maximal selectivity of this reaction, based on the stoichiometry of the reaction equation

cf. Kirk-Othmer's *Encyclopedia of Chemical Technology*, 3$^{rd}$ ed., Vol. 9, 1980, p. 445.

Modern silver-based catalysts however are highly selective towards ethylene oxide production. When using the modern catalysts in the epoxidation of ethylene the selectivity towards ethylene oxide can reach values above the 6/7 or 85.7 mole-% limit referred to. Such highly selective catalysts may comprise as their active components silver, and one or more dopants, such as rhenium, tungsten or molybdenum or a nitrate- or nitrite-forming compound, or components comprising rhenium, tungsten or molybdenum or a nitrate- or nitrite-forming compound. Frequently, the high selectivity catalysts comprise as additional dopants one or more Group IA metals, or one or more components comprising Group IA metals. Preferred Group IA metals are the higher Group IA metals having an atomic number of at least 37, for example rubidium and, in particular, cesium. The Group IA metals having an atomic number of at least 37 may hereinafter be referred to by the term "higher Group IA metals". Highly selective catalysts are disclosed, for example, in U.S. Pat. No. 4,761,394 and U.S. Pat. No. 4,766,105, and in several subsequent patent publications.

The highly selective catalysts are in particular subject to an aging-related performance decline during normal operation and they tend to be exchanged more frequently than the conventional catalysts. The aging manifests itself by a reduction in the activity of the catalyst. Usually, when a reduction in activity of the catalyst is manifest, the reaction temperature is increased in order to compensate for the reduction in activity. The reaction temperature may be increased until it becomes undesirably high, at which point in time the catalyst is deemed to be at the end of its lifetime and would need to be exchanged. It goes without saying that from an economical point of view it is highly desirable to extend the lifetime of the catalyst as much as possible.

SUMMARY OF THE INVENTION

This invention relates to high selectivity catalysts comprising a higher Group IA metal. In accordance with the invention, the initial activity of the catalysts, the performance in the course of the catalysts' lifetime and the lifetime itself are improved when in the preparation of the catalysts a portion of the higher Group IA metal is substituted for potassium.

Accordingly, the present invention provides a catalyst composition comprising a support having a surface area of at least 500 m$^2$/kg, and deposited on the support:
  silver metal,
  a metal or component comprising rhenium, tungsten, molybdenum or a nitrate- or nitrite-forming compound, and
  a Group IA metal or component comprising a Group IA metal having an atomic number of at least 37, and in addition potassium,
wherein the value of the expression $(Q_K/R)+Q_{HIA}$ is in the range of from 1.5 to 30 mmole/kg, wherein $Q_{HIA}$ and $Q_K$ represent the quantities in mmole/kg of the Group IA metal having an atomic number of at least 37 and potassium, respectively, present in the catalyst composition, the ratio of $Q_{HIA}$ to $Q_K$ is at least 1:1, the value of $Q_K$ is at least 0.01 mmole/kg, and R is a dimensionless number in the range of from 1.5 to 5, the units mmole/kg being relative to the weight of the catalyst composition.

The invention also provides a process for preparing a catalyst composition, which process comprises selecting a support having a surface area of at least 500 m$^2$/kg, and depositing on the support:
  silver metal,
  a metal or component comprising rhenium, tungsten, molybdenum or a nitrate- or nitrite-forming compound, and
  a Group IA metal or component comprising a Group IA metal having an atomic number of at least 37, and in addition potassium,
wherein the value of the expression $(Q_K/R)+Q_{HIA}$ is in the range of from 1.5 to 30 mmole/kg, wherein $Q_{HIA}$ and $Q_K$ represent the quantities in mmole/kg of the Group IA metal having an atomic number of at least 37 and potassium, respectively, present in the catalyst composition, the ratio of $Q_{HIA}$ to $Q_K$ is at least 1:1, the value of $Q_K$ is at least 0.01 mmole/kg, and R is a dimensionless number in the range of from 1.5 to 5, the units mmole/kg being relative to the weight of the catalyst composition.

The invention also provides a process for preparing ethylene oxide by reacting ethylene with oxygen in the presence of a catalyst composition according to this invention.

The invention also provides a method of using ethylene oxide for making 1,2-ethanediol, a 1,2-ethanediol ether or an ethanolamine comprising converting ethylene oxide into 1,2-ethanediol, the 1,2-ethanediol ether, or the ethanolamine, wherein the ethylene oxide has been obtained by a process for preparing ethylene oxide according to this invention.

DETAILED DESCRIPTION OF THE INVENTION

The catalyst composition for use in this invention is a supported composition. The support may be selected from a wide range of inert supports. Such supports may be natural or artificial inorganic materials and they include silicon carbide, clays, pumice, zeolites, charcoal and alkaline earth metal carbonates, such as calcium carbonate. Preferred are refractory supports, such as alumina, magnesia, zirconia and silica. The most preferred support is α-alumina.

The support is preferably porous and has a surface area of at least 500 m²/kg, preferably at least 600 m²/kg. Typically, the surface area is less than 5000 m²/kg, more typically at most 4000 m²/kg. As used herein, the surface area is deemed be the B.E.T. surface area as measured by the method as described in Brunauer, Emmet and Teller in *J. Am. Chem. Soc.* 60 (1938) 309-316. The surface area is expressed relative to the weight of the support. A larger surface area may lead to a more active catalyst.

The water absorption of the support is typically at least 0.3 g/g, more typically at least 0.35 g/g. Frequently, the water absorption is at most 0.8 g/g, more frequently at most 0.7 g/g, or at most 0.55 g/g, for example 0.39 g/g, or 0.5 g/g. As used herein, water absorption is as measured in accordance with ASTM C393, and water absorption is expressed as the weight of the water that can be absorbed into the pores of the support, relative to the weight of the support. A higher water absorption and a higher total pore volume are in favour in view of a more efficient deposition of silver and further elements, if any, on the support by impregnation. However, at higher water absorption and higher total pore volume, the support, or the catalyst made therefrom, may have lower crush strength.

The performance of the catalyst composition may be enhanced if the support is washed, to remove soluble residues, before deposition of other catalyst ingredients on the support. On the other hand, unwashed supports may also be used successfully. A useful method for washing the support comprises washing the support in a continuous fashion with hot, demineralised water, until the electrical conductivity of the effluent water does not further decrease. A suitable temperature of the demineralised water is in the range of 80 to 100° C., for example 90° C. or 95° C. Reference may be made to U.S. Pat. No. 6,368,998, US-2002/0010094 A1 and WO-00/15333, which are incorporated herein by reference.

The catalyst composition of this invention comprises silver as a catalytically active metal. Appreciable catalytic activity may be obtained by employing a silver content of at least 10 g/kg, relative to the weight of the catalyst composition. Preferably, the silver content is in the range of from 10 to 500 g/kg, more preferably from 50 to 250 g/kg, for example 105 g/kg, or 130 g/kg, or 200 g/kg, relative to the weight of the catalyst composition.

The preparation of the catalysts is known in the art and the known methods are applicable to the preparation of the catalyst of this invention. Methods of preparing the catalyst include impregnating the support with a silver compound and with other catalyst ingredients, and performing a reduction to form metallic silver particles. Reference may be made, for example, to U.S. Pat. No. 4,761,394, U.S. Pat. No. 4,766,105, U.S. Pat. No. 5,380,697, U.S. Pat. No. 5,739,075, U.S. Pat. No. 6,368,998, US-2002/0010094 A1, WO-00/15333, WO-00/15334 and WO-00/15335, which are incorporated herein by reference.

The impregnation may include impregnation with a solution of which the pH has a value above 12, for example 13 or 13.2 or above. This may be accomplished by the addition of a base to the impregnation solution, for example lithium hydroxide, cesium hydroxide, rubidium hydroxide or a tetraalkylammonium hydroxide, such as tetramethylammonium hydroxide or tetraethylammonium hydroxide, in sufficient quantity. Dependent of the composition of the impregnation solution, a quantity of base in the range of from 20 to 70 mmole/kg catalyst composition, for example 30, 40, 50 or 60 mmole/kg catalyst composition may be sufficient to achieve a sufficiently high pH.

The reduction of cationic silver to metallic silver may be accomplished during a step in which the catalyst composition is dried, so that the reduction as such does not require a separate process step. This may be the case if the impregnation solution comprises a reducing agent, for example, an oxalate, as described in the Examples hereinafter.

The catalyst composition of this invention comprises, in addition to silver, one or more of rhenium, molybdenum, tungsten and nitrate- or nitrite-forming compounds, or components comprising one or more of rhenium, molybdenum, tungsten and nitrate- or nitrite-forming compounds. Preferably, the catalyst comprises rhenium, or a rhenium comprising component. Rhenium, molybdenum and tungsten and nitrate- or nitrite-forming compounds may suitably be provided as an oxyanion, for example, as a perrhenate, molybdate, tungstate, nitrate or nitrite, in salt or acid form. Typically, rhenium, molybdenum, tungsten and/or the nitrate- or nitrite-forming compounds may each be present in a quantity of from 0.01 to 500 mmole/kg, calculated as the element (rhenium, molybdenum, tungsten or nitrogen) on the total catalyst composition. Rhenium may preferably be present in an amount of from 0.1 to 10 mmole/kg, for example 0.2 mmole/kg, or 1.5 mmole/kg, or 2 mmole/kg, or 5 mmole/kg. Tungsten may preferably be present in an amount in the range of from 0.5 to 20 mmole/kg, such as 0.75 mmole/kg, or 5 mmole/kg, or 15 mmole/kg.

As the Group IA metal, the catalyst composition of this invention comprises a higher Group IA metal, and in addition potassium. In accordance with this invention, the quantities of these Group IA metals are such that the value of $(Q_K/R)+Q_{HIA}$ is in the range of from 1.5 to 30 mmole/kg, wherein $Q_{HIA}$ and $Q_K$ represent the quantities of the higher Group IA metal and potassium, respectively, present in the catalyst. $Q_K$ is at least 0.01 mmole/kg, more typically at least 0.1 mmole/kg, relative to the weight of the catalyst composition. Typically, $Q_K$ is at most 50 mmole/kg, more typically at most 30 mmole/kg, relative to the weight of the catalyst composition.

Preferably, the catalyst composition comprises rubidium, and, in particular, cesium as a higher Group IA metal. If cesium is present, cesium may represent at least 75 mole-%, in particular at least 90 mole-%, more particular at least 99 mole-% of the higher Group IA metals. If cesium is present, the other higher Group IA metals (rubidium and francium) may be absent or substantially absent. Preferably, cesium only represents the Group IA metals having an atomic number of at least 37.

R is a dimensionless number in the range of from 1.5 to 5. More typically, the value of R is in the range of from 2 to 3, for example 2.5. A suitable value of R may be determined by routine experimentation, as set out in Examples 1-7, hereinafter, and in the discussion following Examples 1-7.

The ratio of $Q_{HIA}$ to $Q_K$ may be at least 1:1, preferably at least 1.1:1. In preferred embodiments, amongst others, the ratio of $Q_{HIA}$ to $Q_K$ may be at most 5:1, preferably at most 3.5:1, in particular at most 2.5:1, as this leads to a better initial activity, better performance of the catalyst in the course of the lifetime of the catalyst, and to a more extended catalyst lifetime.

It has also been found that for improved initial catalyst activity, improved performance of the catalyst in the course of its lifetime and an improved lifetime of the catalyst, the value of $(Q_K/R)+Q_{HIA}$ may be taken larger as the surface area of the support is larger. In this respect, preferably, the following equation applies:

$$(Q_K/R)+Q_{HIA}=F \times SA,$$

wherein SA denotes the surface area of the support, in m$^2$/kg, and F is a factor having a value in the range of from 0.001 to 0.01 mmole/m$^2$. Typically, the value of F is in the range of from 0.002 to 0.008 mmole/m$^2$. More typically, the value of F is in the range of from 0.003 to 0.006 mmole/m$^2$. Within these ranges the catalyst exhibits an optimum or close to optimum initial activity for a given surface area or for a given value of $(Q_K/R)+Q_{HIA}$.

In the alternative, or more specifically, when the surface area of the support is in the range of from 500 to 1500 m$^2$/kg, in particular from 600 to 1500 m$^2$/kg, the value of $(Q_K/R)+Q_{HIA}$ is preferably in the range of from 1.5 to 12 mmole/kg, in particular from 2 to 6 mmole/kg.

Likewise, when the surface area of the support is in the range of from 1500 to 2500 m$^2$/kg, the value of $(Q_K/R)+Q_{HIA}$ is preferably in the range of from 4 to 15 mmole/kg, in particular from 6 to 10 mmole/kg.

Likewise, when the surface area of the support is in the range of from 2500 to 5000 m$^2$/kg, in particular from 2500 to 4000 m$^2$/kg, the value of $(Q_K/R)+Q_{HIA}$ is preferably in the range of from 5 to 25 mmole/kg, in particular from 10 to 20 mmole/kg.

The catalyst composition of this invention may comprise lithium, as an additional Group IA metal, or a compound thereof. In particular, the catalyst comprises cesium, potassium and lithium as the Group IA metals, other Group IA metals being absent. Suitable amounts for lithium are in the range of from 1 to 500 mmole/kg, more suitably from 5 to 100 mmole/kg, relative to the total weight of the catalyst composition, for example 10 mmole/kg, or 15 mmole/kg, or 40 mmole/kg, or 50 mmole/kg. It is understood that the presence of lithium or a compound thereof on the catalyst surface generally improves the catalyst performance.

Of special preference are catalysts which comprise rhenium, in addition to silver, and further a rhenium co-promoter which may be selected from one or more of sulfur, phosphorus, boron, and components comprising one or more of sulfur, phosphorus and boron, on the support material. Such catalysts are known from U.S. Pat. No. 4,761,394 and U.S. Pat. No. 4,766,105, which are incorporated herein by reference. The rhenium co-promoter may be provided as an oxyanion, in salt or acid form. The rhenium co-promoter or co-promoters may be present in a quantity of from 0.1 to 30 mmole/kg each. Further, a Group IIA metal or a component comprising a Group IIA metal may be present. Suitably each Group IIA metal is present in a quantity of from 0.1 to 500 mmole/kg. The Group IIA metal may be, for example, calcium and barium.

As used herein, the quantity of Group IA metal present in the catalyst composition is deemed to be the quantity in so far as it can be extracted with de-ionized water at 100° C. The extraction method involves extracting a 10-gram sample of the catalyst composition three times by heating it in 20 ml portions of de-ionized water for 5 minutes at 100° C. and determining in the combined extracts the relevant metals by using a known method, for example atomic absorption spectroscopy.

As used herein, the quantity of Group IIA metal present in the catalyst composition is deemed to the quantity in so far as it can be extracted with 10% w nitric acid in de-ionized water at 100° C. The extraction method involves extracting a 10-gram sample of the catalyst composition by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present process for preparing ethylene oxide (hereinafter also referred to as "epoxidation process") may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The ethylene concentration in the feed may be selected within a wide range. Typically, the ethylene concentration in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst.

The present epoxidation process may be air-based or oxygen-based, see "Kirk-Othmer Encyclopedia of Chemical Technology", 3$^{rd}$ edition, Volume 9, 1980, pp. 445-447. In the air-based process air or air enriched with oxygen is employed as the source of the oxidizing agent while in the oxygen-based processes high-purity (at least 95 mole-%) oxygen is employed as the source of the oxidizing agent. Presently most epoxidation plants are oxygen-based and this is a preferred embodiment of the present invention.

The oxygen concentration in the feed may be selected within a wide range. However, in practice, oxygen is generally applied at a concentration which avoids the flammable regime. Typically, the concentration of oxygen applied will be within the range of from 1 to 15 mole-%, more typically from 2 to 12 mole-% of the total feed.

In order to remain outside the flammable regime, the concentration of oxygen in the feed may be lowered as the concentration of ethylene is increased. The actual safe operating ranges depend, along with the feed composition, also on the reaction conditions such as the reaction temperature and the pressure.

A reaction modifier may be present in the feed for increasing the selectively, suppressing the undesirable oxidation of ethylene or ethylene oxide to carbon dioxide and water, relative to the desired formation of ethylene oxide. Many organic compounds, especially organic halides, may be employed as the reaction modifier. Organic nitrogen compounds or inorganic compounds such as nitrogen oxides, hydrazine, hydroxylamine or ammonia may be employed as well, but this is generally less preferred. It is considered that under the operating conditions of the epoxidation process the nitrogen containing reaction modifiers are precursors of nitrates or nitrites, i.e. they are so-called nitrate- or nitrite-forming compounds (cf. e.g. EP-A-3642 and U.S. Pat. No. 4,822,900, which are incorporated herein by reference).

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Suitable nitrogen oxides are of the general formula NO$_x$ wherein x is in the range of from 1 to 2, and include for example NO, N$_2$O$_3$ and N$_2$O$_4$. Suitable organic nitrogen compounds are nitro compounds, nitroso compounds, amines, nitrates and nitrites, for example nitromethane, 1-nitropropane or 2-nitropropane. The nitrate- or nitrite-forming compounds, e.g. nitrogen oxides and/or organic nitrogen compounds, may be used together with an organic halide, in particular an organic chloride.

The reaction modifiers are generally effective when used in low concentration in the feed, for example up to 0.01 mole-%, relative to the total feed. It is preferred that the reaction modifier is present in the feed at a concentration of from $0.1 \times 10^{-4}$ to $50 \times 10^{-4}$ mole-%, in particular from $0.3 \times 10^{-4}$ to $30 \times 10^{-4}$ mole-%, relative to the total feed.

In addition to ethylene, oxygen and the reaction modifier, the feed may comprise one or more optional components, such as carbon dioxide, inert gases and saturated hydrocarbons. Carbon dioxide is a by-product in the epoxidation process. However, carbon dioxide generally has an adverse effect on the catalyst activity. Typically, a concentration of carbon dioxide in the feed in excess of 25 mole-%, preferably in excess of 10 mole-%, relative to the total feed, is avoided. A concentration of carbon dioxide as low as 0.5 mole-% or lower, relative to the total feed, may be employed, for example in the range of from 0.5 to 4 mole-%, in particular from 0.5 to 2 mole-%, relative to the total feed. Inert gases, for example nitrogen or argon, may be present in the feed in a concentration of from 30 to 90 mole-%, typically from 40 to 80 mole-%. Suitable saturated hydrocarbons are methane and ethane. If saturated hydrocarbons are present, they may be present in a quantity of up to 80 mole-%, relative to the total feed, in particular up to 75 mole-%. Frequently they are present in a quantity of at least 30 mole-%, more frequently at least 40 mole-%. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is as a gas phase process involving a packed catalyst bed, the GHSV is in the range of from 1000 to 10000 Nl/(l·h). Preferably, the process is carried out at a work rate in the range of from 0.5 to 10 kmole ethylene oxide produced per $m^3$ of catalyst per hour, in particular 0.7 to 8 kmole ethylene oxide produced per $m^3$ of catalyst per hour, for example 5 kmole ethylene oxide produced per $m^3$ of catalyst per hour. As used herein, the work rate is the amount of ethylene oxide produced per unit volume of catalyst per hour and the selectivity is the molar quantity of ethylene oxide formed relative to the molar quantity of ethylene converted.

The ethylene oxide produced may be recovered from the reaction mixture by using methods known in the art, for example by absorbing the ethylene oxide from a reactor outlet stream in water and optionally recovering the ethylene oxide from the aqueous solution by distillation. At least a portion of the aqueous solution containing the ethylene oxide may be applied in a subsequent process for converting the ethylene oxide into 1,2-ethanediol or a 1,2-ethanediol ether.

The ethylene oxide produced in the epoxidation process may be converted into 1,2-ethanediol, a 1,2-ethanediol ether, or an ethanolamine. As this invention leads to a more attractive process for the production of ethylene oxide, it concurrently leads to a more attractive process which comprises producing ethylene oxide in accordance with the invention and the subsequent use of the obtained ethylene oxide in the manufacture of the 1,2-ethanediol, 1,2-ethanediol ether, and/or ethanolamine.

The conversion into 1,2-ethanediol or the 1,2-ethanediol ether may comprise, for example, reacting the ethylene oxide with water, suitably using an acidic or a basic catalyst. For example, for making predominantly 1,2-ethanediol and less 1,2-ethanediol ether, the ethylene oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-ethanediol ethers in the reaction mixture is increased. The 1,2-ethanediol ethers thus produced may be a di-ether, tri-ether, tetra-ether or a subsequent ether. Alternative 1,2-ethanediol ethers may be prepared by converting the ethylene oxide with an alcohol, in particular a primary alcohol, such as methanol or ethanol, by replacing at least a portion of the water by the alcohol.

The conversion into the ethanolamine may comprise, for example, reacting the ethylene oxide with ammonia. Anhydrous or aqueous ammonia may be used, although anhydrous ammonia is typically used to favour the production of monoethanolamine. For methods applicable in the conversion of the ethylene oxide into the ethanolamine, reference may be made to, for example U.S. Pat. No. 4,845,296, which is incorporated herein by reference.

The 1,2-ethanediol and the 1,2-ethanediol ether may be used in a large variety of industrial applications, for example in the fields of food, beverages, tobacco, cosmetics, thermoplastic polymers, curable resin systems, detergents, heat transfer systems, etc. The ethanolamine may be used, for example, in the treating ("sweetening") of natural gas.

Unless specified otherwise, the low-molecular weight organic compounds mentioned herein, for example the 1,2-ethanediol ethers and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

The following examples will illustrate the invention.

Examples 1-9

Examples 3-5 According to the Invention, Examples 1, 2 and 6-9 for Comparison

Preparation of a Support

An α-alumina support was prepared according to the process as described in Example 1 of U.S. Pat. No. 5,100,859. The surface area of the support was 790 $m^2$/kg, the water absorption was 0.39 g/g.

Preparation of Catalysts

A silver-amine-oxalate stock solution was prepared by the following procedure:

415 g of reagent-grade sodium hydroxide were dissolved in 2340 ml de-ionized water and the temperature was adjusted to 50° C.

1699 g high purity "Spectropure" silver nitrate was dissolved in 2100 ml de-ionized water and the temperature was adjusted to 50° C.

The sodium hydroxide solution was added slowly to the silver nitrate solution, with stirring, while maintaining a solution temperature of 50° C. This mixture was stirred for 15 minutes, then the temperature was lowered to 40° C.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml fresh deionized water was then added.

630 g of high-purity oxalic acid dihydrate were added in approximately 100 g increments. The temperature was keep at 40° C. and the pH was kept above 7.8.

Water was removed from this mixture to leave a highly concentrated silver-containing slurry. The silver oxalate slurry was cooled to 30° C.

699 g of 92% w ethylenediamine (8% w de-ionized water) was added while maintaining a temperature no greater than 30° C. Water was added to obtain a solution having a density of 1.5-1.55 g/ml at 20° C. The resulting silver-amine-oxalate stock solution contained approximately 28-30% w silver.

Impregnation solutions were prepared by adding aqueous solutions comprising predetermined quantities of lithium nitrate, ammonium perrhenate, ammonium metatungstate, cesium hydroxide (optional), potassium nitrate (optional), and water to samples of an silver-amine-oxalate stock solution as described. The quantities were predetermined by calculation based on the desired composition of the catalyst to be prepared.

Samples of the support, prepared as indicated under the heading "Preparation of Supports", were impregnated with the impregnation solutions and dried, as follows. The support samples (each approximately 30 g) were placed under a 25 mm Hg vacuum for 1 minute at ambient temperature. Approximately 50 g of an impregnating solution, prepared as indicated hereinbefore, was then introduced to submerse the support, and the vacuum was maintained at 25 mm Hg for an additional 3 minutes. The vacuum was then released and the excess impregnating solution was removed from the catalyst pre-cursor by centrifugation at 500 rpm for two minutes. The catalyst pre-cursor was then dried while being shaken at 250° C. for 5.5 minutes in a stream of air. The catalysts so prepared contained 13.2% w silver, 1.5 mmole/kg rhenium, 0.75 mmole/kg tungsten and 15 mmole/kg lithium and they had cesium and potassium loadings as specified in Table I, hereinafter, all relative to the weight of the catalysts.

Catalyst Testing

The catalysts so prepared were tested in the production of ethylene oxide from ethylene and oxygen. To do this, 3.5 to 4.5 g of crushed catalyst were loaded into a stainless steel U-shaped tube. The tube was immersed in a molten metal bath (heat medium) and the ends were connected to a gas flow system. A gas or gas mixture passed through the catalyst bed, in a "once-through" operation. The weight of catalyst used and the inlet gas flow rate were adjusted to give a gas hourly space velocity of 3300 Nl/(l·h). The inlet gas pressure was 1550 kPa absolute.

First, the catalysts were pretreated at 225° C. for 3 hours with nitrogen, and then the composition of the gas mixture was adjusted to 30% v ethylene, 8% v oxygen, 5% v carbon dioxide, 2.5 ppmv ethyl chloride, and nitrogen balance.

The reactor temperature was ramped up at a rate of 10° C. per hour to 245° C. and then the temperature was adjusted so as to achieve an ethylene oxide content of 3.1% v in the outlet gas stream. The ethyl chloride concentration in the gas mixture was adjusted between 2.5 and 5 ppmv so as to obtain an optimum selectivity at a constant ethylene oxide concentration in the outlet gas stream. The temperature was slowly increased to compensate for a decline in catalyst performance as a result of ageing, i.e. such that a constant ethylene oxide content in the outlet gas stream was maintained.

For the catalysts the performance values for selectivity and temperature are reported in Table I, hereinafter. A lower temperature needed to accomplish a certain ethylene oxide (EO) content in the outlet gas stream is indicative for a higher activity of the catalyst.

TABLE I

| | | Example | | | | | | | | |
|---|---|---|---|---|---|---|---|---|---|---|
| | | 1 *) | 2 *) | 3 **) | 4 **) | 5 **) | 6 *) | 7 *) | 8 *) | 9 *) |
| Catalyst composition (mmole/kg) | Potassium content | 0 | 0 | 1 | 1.5 | 2 | 2.5 | 3.5 | 2 | 0 |
| | Cesium content | 3 | 3.4 | 3 | 2.6 | 2.6 | 2.3 | 1.7 | 0 | 2.6 |
| Initial performance | Temperature (° C.) | 256 | 257 | 253 | 252 | 251 | 255 | 255 | 249 | 249 |
| | Selectivity (% mole) | 87.6 | 87.7 | 86.9 | 84.7 | 86.3 | 86.0 | 83.6 | 59.4 | 84.7 |
| Performance at cumulative EO production of | 160 T/m³ Temperature (° C.) | 257 | 258 | 259 | 258 | 254 | 263 | 263 | | |
| | Selectivity (% mole) | 88 | 87.6 | 88 | 88.5 | 86.1 | 86.6 | 86 | | |
| | 530 T/m³ Temperature (° C.) | | | | | | | 279 | | |
| | Selectivity (% mole) | | | | | | | 84.8 | | |
| | 580 T/m³ Temperature (° C.) | | | | | | | 278 | | |
| | Selectivity (% mole) | | | | | | | 86.5 | | |
| | 640 T/m³ Temperature (° C.) | 267 | 277 | 267 | 270 | 267 | | | | |
| | Selectivity (% mole) | 86 | 85.8 | 86.8 | 87.2 | 87.2 | | | | |
| | 960 T/m³ Temperature (° C.) | 280 | | 278 | 274 | 274 | | | | |

TABLE I-continued

| | | Example | | | | | | | | |
|---|---|---|---|---|---|---|---|---|---|---|
| | | 1 *) | 2 *) | 3 **) | 4 **) | 5 **) | 6 *) | 7 *) | 8 *) | 9 *) |
| | Selectivity (% mole) | 82.2 | | 84.7 | 86.8 | 85.8 | | | | |
| 1600 T/m³ | Temperature (° C.) | 293 | | 295 | | 296 | | | | |
| | Selectivity (% mole) | 74.4 | | 77.3 | | 80.1 | | | | |

*) comparative
**) invention
empty space: not measured

The cesium content of the catalysts of Examples 1 and 2 were chosen such that the initial performance of the catalysts was approximately at optimum. It appeared that, starting from the catalyst of Example 2, by substituting cesium in part by potassium while keeping the value of $(Q_K/2.5)+Q_{HIA}$ approximately constant (i.e. R equals 2.5), catalysts could be prepared which were at optimum initial activity for the chosen quantity of cesium and, furthermore, that the (optimum) initial activities of these catalysts were higher than the initial activity of the catalysts of Examples 1 and 2 (compare: initial activities 253° C., 252° C., 251° C., 255° C., 255° C. in Examples 3-7, with initial activities 256° C. and 257° C. in Examples 1 and 2).

The Examples further show that at a prolonged use of the catalysts, for example at a cumulative ethylene oxide production of at least 160 T/m³ catalyst, the catalysts according to the invention exhibit very advantageously an improved activity and selectivity, relative to the comparative catalysts (for example, compare: activity 267° C. and selectivity 87.2 mole-% at an cumulative ethylene oxide production of 640 T/m³ in Example 5, with 277° C. and 85.8 mole-% at 640 T/m³ in Example 2, and 278° C. and 86.5 mole-% at 580 T/m³ in Example 6). In particular, the improved long-term selectivity of the catalyst according to the invention is unexpected, in view of the fact that its initial selectivity is not the best.

Generically, the value of R may be determined by routine experimentation, by determining for a highly selective catalyst the value of $Q_{HIA}$ (if more than one higher Group IA metal is present, at a constant ratio of the molar quantities of the individual higher Group IA metals) at which the catalysts exhibits optimal initial activity, and then determining the rate R at which a portion of the one higher Group IA metal (if more than one higher Group IA metal is present, at the same ratio of the molar quantities of the individual higher Group IA metals) may be substituted by potassium such that the catalyst remains exhibiting an optimum initial activity. The value of R may be determined by measuring initial activities in the epoxidation of ethylene to ethylene oxide, by using an experimental set-up as provided in Examples 1-7, whereby, as used throughout in this patent document, the initial activity is the highest activity found at an cumulative ethylene oxide production of less than 160 T/m³ catalyst.

The fact that the value of R can be determined by routine experimentation which involves starting from catalysts which are optimised for their initial activity with respect to their contents of higher Group IA metal, does not imply that the optimisation of the initial activity is an essential feature of this invention. For example, when from a catalyst similar to the catalyst of Example 1, except for having a different (i.e. non-optimal) cesium content, a portion of the cesium would be substituted by potassium, at a rate of 2.5 mmole potassium per mmole cesium substituted (i.e. R equals 2.5), in accordance with this invention, the resulting catalyst will be advantaged, in that it exhibits a higher initial activity and its performance in the course of its lifetime and the lifetime itself are improved, similar as found for the catalyst of Example 2, compared with the catalyst of Example 1.

Example 10

According to the Invention

An α-alumina support was prepared by mixing the following ingredients:
1. 67.4 parts by weight (pbw) of an α-alumina with $d_{50}$ of 29 μm;
2. 29 pbw of an α-alumina with $d_{50}$ of 3 μm;
3. 3 pbw of aluminium oxide (in the form of boehmite);
4. 0.5 pbw of silica (in the form of ammonia stabilized silica sol); and
5. 0.1 pbw of sodium oxide (in the form of sodium acetate).

The average particle size, referred to herein as "$d_{50}$", is as measured by a Horiba LA900 particle size analyzer and represents a particle diameter at which there are equal spherical equivalent volumes of particles larger and particles smaller than the stated average particle size. The method includes dispersing the particles by ultrasonic treatment, thus breaking up secondary particles into primary particles. This sonification treatment is continued until no further change in the $d_{50}$ value is noticed, which typically requires 5 minute sonification when using the Horiba LA900 particle size analyzer.

To this mixture were added 5% w, relative to the mixture weight, of petroleum jelly and 9% w, relative to the mixture weight, of burnout material and 0.1% w, relative to the mixture weight, of boric acid. Water (about 30% w, relative to the mixture weight) was then added in an amount to make the mixture extrudable and this mixture was then extruded to form formed bodies in the form of hollow cylinders that are about 8 mm in diameter and 8 mm long. These were then dried and fired in a kiln at 1425° C., for 4 hours in air to produce Support A. As regards procedures followed in this support preparation, reference may be made to U.S. Pat. No. 5,100,859.

The surface area of the support so prepared was 2000 m²/kg, the water absorption was 0.42 g/g.

The support was subjected to washing with boiling deionised water following the method as disclosed in US-2002/0010094 A1, paragraph 0034. The dried support was then used for the preparation of a catalyst by the procedures applied in the Preparation of Catalysts, specified in Examples 1-9. The catalyst so prepared contained 13.2% w silver, 2 mmole/kg rhenium, 1 mmole/kg tungsten, 6.4 mmole/kg cesium, 4 mmole/kg potassium and 40 mmole/kg lithium, relative to the weight of the catalyst. The catalyst was tested using the procedures outlined in Examples 1-9. The results are given in Table II.

TABLE II

| | Performance at cumulative EO production of | | | | |
|---|---|---|---|---|---|
| Initial performance | | 160 T/m³ | | | |
| Temperature (° C.) | Selectivity (mole-%) | Temperature (° C.) | Selectivity (mole-%) | 640 T/m³ Temperature (° C.) | Selectivity (mole-%) |
| 244 | 87.9 | 245 | 87.6 | 245 | 86.2 |

What is claimed is:

1. A process for preparing a catalyst composition, which process comprises selecting a support having a surface area in the range of from 500 m²/kg to less than 5000 m²/kg, and depositing on the support:
   silver metal,
   rhenium, or a component comprising rhenium, in an amount greater than 1.5 mmole/kg,
   a Group IA metal having an atomic number of at least 37, or a component comprising a Group IA metal having an atomic number of at least 37, wherein the Group IA metal having an atomic number of at least 37 is cesium,
   lithium, or a component comprising lithium, in an amount in the range of from 1 to 500 mmole/kg, relative to the total weight of the catalyst composition, and
   potassium, or a component comprising potassium;
such that the value of the expression $(Q_K/R)+Q_{HIA}$ is in the range of from 1.5 to 30 mmole/kg, wherein $Q_{HIA}$ and $Q_K$ represent the amounts in mmole/kg, relative to the total weight of the catalyst composition, of the Group IA metal having an atomic number of at least 37 and potassium, respectively, present in the catalyst composition, and R is a dimensionless number in the range of from 1.5 to 5; and wherein the ratio of $Q_{HIA}$ to $Q_K$ is in the range of from 1:1 to 3.5:1.

2. The process as claimed in claim 1, wherein the value of R is 2.5 and the ratio of $Q_{HIA}$ to $Q_K$ is in the range of from 1.1:1 to 2.5:1.

3. The process as claimed in claim 1, wherein the ratio of $Q_{HIA}$ to $Q_K$ is in the range of from 1.1:1 to 2.5:1.

4. The process as claimed in claim 1, wherein the following equation applies:

$$(Q_K/R)+Q_{HIA}=F \times SA,$$

where SA is the surface area of the support, in m²/kg, and F is a factor having a value in the range of from 0.001 to 0.01 mmole/m².

5. The process as claimed in claim 4, wherein the value of F is in the range of from 0.002 to 0.008 mmole/m².

6. The process as claimed in claim 1, wherein
   the surface area of the support is in the range of from 500 to 1500 m²/kg, and the value of $(Q_K/R)+Q_{HIA}$ is in the range of from 1.5 to 12 mmole/kg; or
   the surface area of the support is in the range of from 1500 to 2500 m²/kg, and the value of $(Q_K/R)+Q_{HIA}$ is in the range of from 4 to 15 mmole/kg; or
   the surface area of the support is in the range of from 2500 to 5000 m²/kg, and the value of $(Q_K/R)+Q_{HIA}$ is in the range of from 5 to 25 mmole/kg.

7. The process as claimed in claim 1, wherein the process further comprises depositing on the support a rhenium co-promoter, or a component comprising the rhenium co-promoter, wherein the rhenium co-promoter is selected from the group consisting of sulfur, phosphorus, boron, and a combination thereof.

8. The process as claimed in claim 1, wherein the surface area of the support is in the range of from 500 to 1500 m²/kg, and the value of $(Q_K/R)+Q_{HIA}$ is in the range of from 2 to 6 mmole/kg.

9. The process as claimed in claim 1, wherein the amount of lithium deposited is in the range of from 1 to 100 mmole/kg, relative to the total catalyst composition.

10. The process as claimed in claim 1, wherein the amount of lithium deposited is in the range of from 5 to 50 mmole/kg, relative to the total weight of the catalyst composition.

11. The process as claimed in claim 1, wherein the surface area of the support is in the range of from 500 to 2500 m²/kg and the value of $(Q_K/R)+Q_{HIA}$ is in the range of from 1.5 to 10.

12. The process as claimed in claim 1, wherein the ratio of $Q_{HIA}$ to $Q_K$ is in the range of from 1.1:1 to 2.5:1.

13. The process as claimed in claim 4, wherein the value of F is in the range of from 0.003 to 0.006 mmole/m².

14. The process as claimed in claim 1, wherein the rhenium, or the component comprising rhenium, is deposited on the support in an amount in the range of from 1.5 to 5 mmole/kg, calculated as the amount of rhenium relative to the total weight of the catalyst composition.

15. The process as claimed in claim 1, wherein the process further comprises depositing on the support molybdenum, or a component comprising molybdenum.

16. The process as claimed in claim 1, wherein the process further comprises depositing on the support tungsten, or a component comprising tungsten.

17. The process as claimed in claim 15, wherein the molybdenum, or the component comprising tungsten, is deposited on the support in an amount in the range of from 0.5 to 20 mmole/kg, calculated as the amount of molybdenum relative to the total weight of the catalyst composition.

18. The process as claimed in claim 16, wherein the tungsten, or the component comprising tungsten, is deposited on the support in an amount in the range of from 0.5 to 5 mmole/kg, calculated as the amount of tungsten relative to the total weight of the catalyst composition.

19. The process as claimed in claim 1, wherein R is in the range of from 2 to 3.

20. The process as claimed in claim 1, wherein the surface area of the support is in the range of 1500 to 2500 m²/kg, and the value of $(Q_K/R)+Q_{HIA}$ is in the range of from 4 to 15 mmole/kg.

21. The process as claimed in claim 1, wherein the surface area of the support is in the range of from 2500 to 5000 m²/kg, and the value of $(Q_K/R)+Q_{HIA}$ is in the range of from 5 to 25 mmole/kg.

* * * * *